US012041989B2

(12) United States Patent
Rubio et al.

(10) Patent No.: US 12,041,989 B2
(45) Date of Patent: Jul. 23, 2024

(54) SAFER SHIELD COPPER INFUSED GRAPHENE FACE MASK

(71) Applicants: Rey Jesus Rubio, Miami, FL (US); Jeffrey Matthew Childers, Miami, FL (US)

(72) Inventors: Rey Jesus Rubio, Miami, FL (US); Jeffrey Matthew Childers, Miami, FL (US)

(*) Notice: Subject to any disclaimer, the term of this patent is extended or adjusted under 35 U.S.C. 154(b) by 699 days.

(21) Appl. No.: 17/220,648

(22) Filed: Apr. 1, 2021

(65) Prior Publication Data

US 2021/0307430 A1     Oct. 7, 2021

Related U.S. Application Data

(60) Provisional application No. 63/003,865, filed on Apr. 1, 2020.

(51) Int. Cl.
*A41D 13/11* (2006.01)
*B01D 46/00* (2022.01)

(52) U.S. Cl.
CPC ...... *A41D 13/1192* (2013.01); *B01D 46/0028* (2013.01); *B01D 2239/025* (2013.01); *B01D 2239/0258* (2013.01)

(58) Field of Classification Search
CPC ..................................... A41D 13/11
See application file for complete search history.

(56) References Cited

FOREIGN PATENT DOCUMENTS

KR        101880532 B1 *  6/2017

* cited by examiner

*Primary Examiner* — Kim M Lewis

(57) ABSTRACT

A reusable face mask for covering the mouth and nose of a wearer to prevent the passage of pathogenic biological airborne particulates. The mask has three layers including a filter material made of graphene and infused with activated copper carbon. A Bluetooth transmitter wirelessly transmits a continuous frequency of 2.4 GHz to destroy and prevent the passage of any human pathogens from entering, while freely allowing the passage of air in both directions.

6 Claims, 1 Drawing Sheet

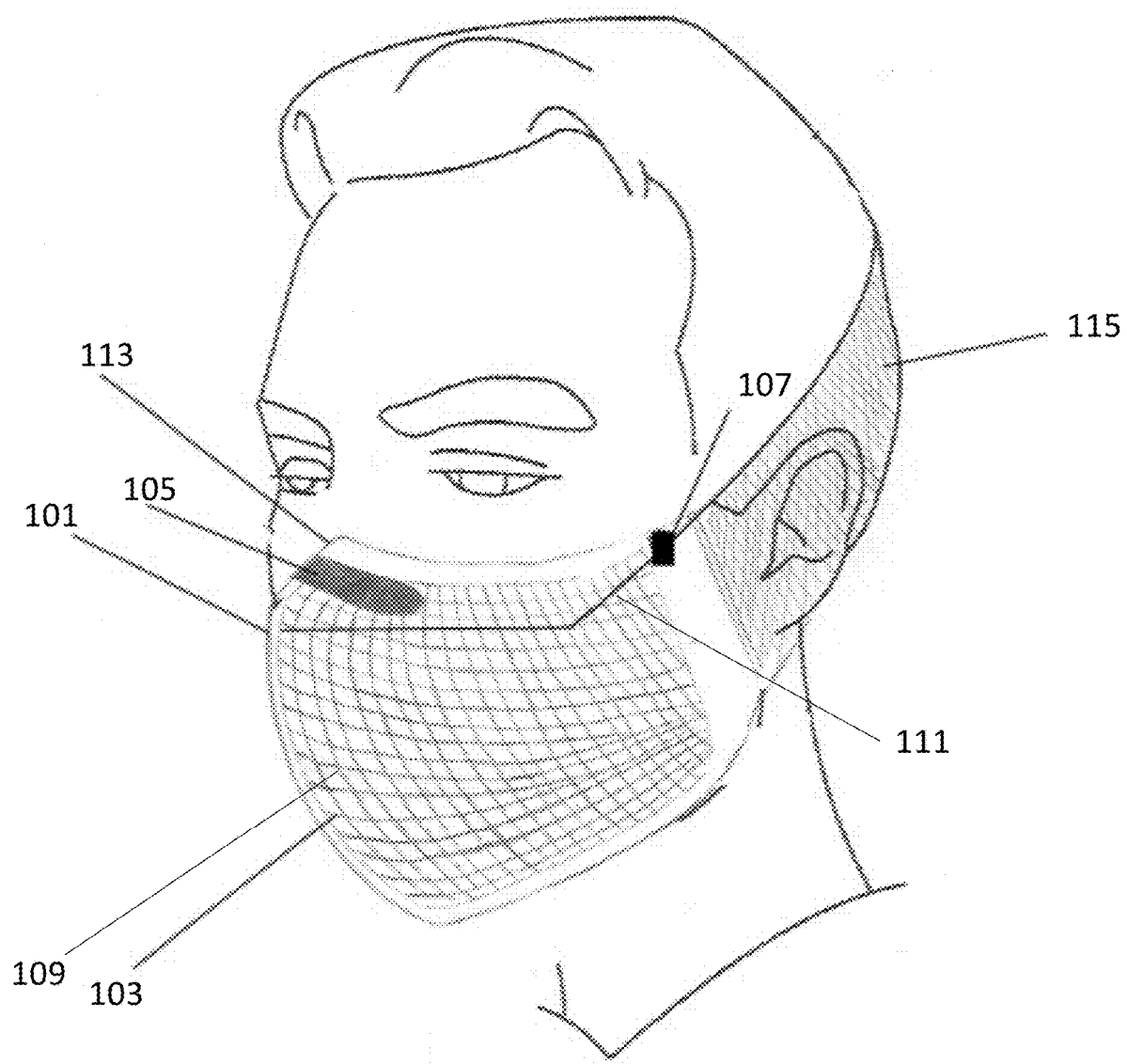

SAFER SHIELD COPPER INFUSED GRAPHENE FACE MASK

CROSS REFERENCE TO RELATED APPLICATION

This application claims the benefit of U.S. Provisional Application No. 63/003,865 filed on Apr. 1, 2020, the disclosures of which are hereby incorporated herein by reference in their entirety.

FIELD OF THE INVENTION

The present invention relates generally to the field of personal face masks and personal protective equipment. More particularly, the invention relates to a face mask with a filtering respirator using copper infused graphene that reduces wearer exposure to pathogenic biological airborne particulates.

BACKGROUND

Due to the current global COVID-19 pandemic, now more than ever individuals need protective gear that will allow them to breathe clean, safe, virus-free, bacteria-free and infection-free air. Personal face masks have been used in many industries from the medical field to the construction industry and even janitorial services. Usually, the filtration device consists of paper or fiber material. The basic mechanism uses human inhalation to suck air through the filter media and stop all potentially harmful particles from being inhaled by the wearer. The filtration system essentially blocks the foreign matter from entering the user's airways, but does nothing to kill any harmful particulates that happen to succeed in passing through the filter. Likewise, the filtration function is usually less efficient during exhalation because air often leaks through the edges of the mask by the mouth or nose of the wearer, rather than flowing through the filter thereby blocking the passage of contaminated air onto third parties that the user may come in contact with. An effective filtration system will eliminate any contaminated air including airborne particles, bacteria and/or viruses. The present invention provides such a filtration system by incorporating graphene, copper and a Bluetooth transmitter that will not only block the passage of any harmful particulates, but actually kill them, making the filtration system much safer for the user.

Graphene is an allotrope of carbon in the form of a single layer of atoms in a two-dimensional hexagonal lattice in which one atom forms each vertex. It is the basic structural element of other allotropes, including graphite, charcoal, carbon nanotubes and fullerenes. Graphene is a crystalline allotrope of carbon with two-dimensional properties. Its carbon atoms are densely packed in a regular atomic-scale chicken wire (hexagonal) pattern. Graphene is incredibly strong (stronger than steel), naturally antibacterial, resistant, flexible, transparent, highly conductive, and seemingly impermeable to most gases and liquids. Scientists at Cambridge demonstrated that graphene can act as a superconductor (a material with no electrical resistance) when paired with praseodymium cerium copper oxide, researchers at MIT discovered another astounding property: It can apparently function as a superconductor alone, in the right configuration. Materials that conduct heat very well also conduct electricity well, because both processes transport energy using electrons. The flat, hexagonal lattice of graphene offers relatively little resistance to electrons, which zip through it quickly and easily, carrying electricity better than even superb conductors such as copper and almost as well as superconductors (unlike superconductors, which need to be cooled to low temperatures, graphene's remarkable conductivity works even at room temperature). On the other hand, if you pepper tiny holes into graphene to make it porous, you get make a mesh-like material called holey graphene that can work like an electrical semiconductor or a very fine, physical sieve. Filtration is one of graphene's most obvious uses. Sheets of graphene have such closely knit carbon atoms that they can work like super-fine atomic nets, stopping other materials from getting through. Graphene's tight atomic bonds make it impermeable for nearly all gasses and liquids. Curiously, water molecules are an exception. Because water can evaporate through graphene while most other gasses and liquids cannot, graphene could be an exceptional tool for filtration. In a study published by The Royal Society of Chemistry, researchers showed that oxidized graphene could even pull in radioactive materials such as uranium and plutonium present in water, leaving the liquid free of contaminants. Graphite nanoplatelets integrated into plastic medical surfaces can prevent infections, killing 99.99 percent of bacteria which try to attach to it. Similarly, due to its two-dimensional structure, sharp edges, and negatively charged surfaces, a graphene oxide nanosheet is capable of interacting with microorganisms such as bacteria and viruses and destroying them by disrupting their plasma membrane or by generating reactive oxygen species to induce oxidative stress.

Like many respiratory viruses, including the flu, COVID-19 can be spread in tiny droplets released from the nose and mouth of an infected person as they cough. A single cough can produce up to 3,000 droplets. These particles can land on other people, clothing and surfaces around them, but some of the smaller particles can remain in the air. Droplet transmission is typically limited to short distances, but airborne particles are much smaller and can float and move longer distances with air currents. Under certain humidity and temperature environments, airborne droplets can remain in flight for hours. The antimicrobial efficacy of uncoated copper and copper alloy surfaces have proven to kill human pathogens, including one strain of the coronavirus. Copper and copper alloys like brass, bronze, and copper-nickel, have long been known to have health benefits. Some of these metals are even naturally antimicrobial. Research has shown that copper kills certain viruses on contact by degrading them. In 2015, researchers compared infection rates at three hospitals and found that when copper alloys were used in hospitals, it reduced infection rates by 58%. When influenzas, bacteria like *E. coli*, superbugs like MRSA, or even coronaviruses land on most hard surfaces, they can live for up to four to five days. But when they land on copper, and copper alloys like brass, they begin to die within minutes and are undetectable within hours.

SUMMARY

The following presents a simplified summary of the disclosure in order to provide a basic understanding of some aspects of the disclosure. This summary is not an extensive overview of the disclosure. Rather than specifically identifying key or critical elements of the disclosure or to delineate the scope of the disclosure, its purpose, inter alia, is to present some concepts of the disclosure in a simplified form as a prelude to the more detailed description that is presented later.

The invention relates to a multi-layered mask with a filtration system made up of graphene, copper and a Bluetooth transmitter. The outside layer consists of black ballistic nylon (1 micron filtration); a second layer consists of activated copper carbon containment in 1 micron filter fabric; a third layer consists of a 0.5 micron polypropylene mesh. The mask utilizes a Bluetooth transmitter which allows 2.4 GHz frequency to pass through the copper carbon continuously so that the charge destroys any virus and/or bacteria that comes in contact with the filter. The mask is tethered with bungee cords that loop around the user's ears to keep the mask securely covering the wearer's nose and mouth.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following description of the invention when considered in conjunction with the drawings.

BRIEF DESCRIPTION OF THE DRAWINGS

The drawings, in which like numerals represent similar parts, illustrate generally, by way of example, but not by way of limitation, various embodiments discussed in the present document.

FIG. 1. FIG. 1 illustrates the overall schematic of the face mask in accordance with one implementation or embodiment.

DETAILED DESCRIPTION AND BEST MODE OF IMPLEMENTATION

The foregoing summary, as well as the following detailed description of certain embodiments of the subject matter set forth herein, will be better understood when read in conjunction with the appended drawings. In the following detailed description, reference is made to the accompanying drawings which form a part hereof, and in which are shown by way of illustration specific embodiments in which the subject matter disclosed herein may be practiced. These embodiments, which are also referred to herein as "examples," are described in sufficient detail to enable those skilled in the art to practice the subject matter disclosed herein. It is to be understood that the embodiments may be combined or that other embodiments may be utilized, and that variations may be made without departing from the scope of the subject matter disclosed herein. Furthermore, references to "one embodiment" are not intended to be interpreted as excluding the existence of additional embodiments that also incorporate the recited features. The following detailed description is, therefore, not to be taken in a limiting sense, and the scope of the subject matter disclosed herein is defined by the appended claims and their equivalents.

FIG. 1 illustrates an outer layer of ballistic nylon 101, a micron mesh bag 103, with graphene infused plastic 105, a Bluetooth transmitter 107, copper mesh infused with graphene oxide 109, copper wire 111, a layer of neoprene 113, and a full ear cover made of neoprene 115.

What is claimed is:

1. A multi-layered face mask of a shape suitable to be placed over a user's mouth and nose, provided with a means for holding the mask in place on the user's face, having a copper infused graphene filtration system consisting of:
   a first layer made of 5-ply double ballistic nylon with passive carbon grease filter, which can filter particles up to one micron in diameter;
   a second layer having an individualized copper graphene oxide filter with an activated copper carbon containment in a fabric which can filter particles up to one micron in diameter;
   a third layer comprised of a polypropylene copper mesh infused felt which can filter particles up to 0.5 micron in diameter;
   a copper wire trim running along the top of the mask from end to end;
   a short-ranged wireless transmitter embedded within the first, second and third layers;
   a microchip;
   a microphone;
   a UV light; and
   a neoprene covered bungee cord.

2. The multi-layered face mask of claim 1, wherein the microchip transmits a frequency of 2.4 GHz continuously through the copper carbon containment.

3. The multi-layered face mask of claim 1, wherein the microchip transmits a reading of air cleanliness and bacteria killed.

4. The multi-layered face mask of claim 1, wherein the microphone connects to the short-ranged wireless transmitter and projects through user's phone or mobile device.

5. The multi-layered face mask of claim 1, wherein the UV light acts as a sterilizer to filter the air passing through the mask.

6. The multi-layered face mask of claim 1, wherein the polypropylene copper mesh infused felt further comprises:
   finely chopped copper;
   hydrochloric acid; and
   graphene oxide;
   wherein a covalent bond formed by the sharing of electrons naturally occurring in the finely chopped copper and the graphene oxide, coupled with a valence electron of oxygen in the oxygen atom's outermost shell, create a photosynthesis effect that produces oxygen for the user.

* * * * *